US00PP29636P2

(12) United States Plant Patent
Cho

(10) Patent No.: US PP29,636 P2
(45) Date of Patent: Sep. 4, 2018

(54) ***LEUCADENDRON* PLANT NAMED 'HAWAII MAGIC'**

(50) Latin Name: ***Leucadendron salignum* x *discolor***
Varietal Denomination: Hawaii Magic

(71) Applicant: University of Hawaii, Honolulu, HI (US)

(72) Inventor: John J. Cho, Paia, HI (US)

(73) Assignee: University of Hawaii, Honolulu, HI (US)

( * ) Notice: Subject to any disclaimer, the term of this patent is extended or adjusted under 35 U.S.C. 154(b) by 0 days.

(21) Appl. No.: 15/530,967

(22) Filed: Mar. 29, 2017

(51) Int. Cl.
*A01H 5/00* (2018.01)

(52) U.S. Cl.
USPC ..... Plt./226
CPC ..... *A01H 5/00* (2013.01)

(58) Field of Classification Search
USPC ..... Plt./226
CPC ..... A01H 5/00; A01H 5/02
See application file for complete search history.

(56) References Cited

PUBLICATIONS http://planthaven.com/plant/leucadendron-royal-hawaiian-hawaii-magic/leucadendron-hawaii-magic-001/; Oct. 13, 2016; 1 page.*

* cited by examiner

*Primary Examiner* — Kent L Bell
(74) *Attorney, Agent, or Firm* — Bethany R. Roahrig; Barbara Campbell; Cochran Freund & Young LLC

(57) ABSTRACT

A new cultivar of *Leucadendron* plant named 'Hawaii Magic' that is distinguished by compact bushy plant habit, foliage color which changes from olive green in summer months to orange-red in the fall and becoming plum colored in spring. The branch stems of 'Hawaii Magic' are bright red in color. 'Hawaii Magic' bears only male flowers which are yellow in color.

3 Drawing Sheets

Genus and species: *Leucadendron salignum* x *discolor*.
Variety denomination: 'Hawaii Magic'.

BACKGROUND OF THE NEW PLANT

The present invention relates to a new variety of *Leucadendron salignum* x *discolor*, hereinafter referred to by the cultivar name 'Hawaii Magic'. 'Hawaii Magic' is a hybrid selection which originated from the inventor's breeding program in Kula, Hi. The genus *Leucadendron* is a member of the Proteaceae or Protea family which is a significant commercial class of Mediterranean plants used as cut flowering stems and ornamental container plants.

The inventor commenced his *Leucadendron* breeding program in 2011. The objective of the breeding program to develop small or dwarf types of Protea for the worldwide container ornamental plant market with novel foliage colors, superior growth habits for commercial cultivation and for home gardener use.

In 2012, the inventor carried out controlled pollination between an unnamed and upatented plant of *Leucadendron discolor* as the male parent and *Leucadendron salignum* 'Red Devil' (unpatented) as female parent. 'Hawaii Magic' was selected as an individual plant in 2013 for its bright yellow flowers and naturally compact and branching and secondary branching habit.

The inventor first asexually propagated 'Hawaii Magic' in 2013 in Kula, Hi. using semi-ripe tip cuttings. 'Hawaii Magic' has been found to remain stable and uniform and to reproduce true to type in successive generations of asexual reproduction. 'Hawaii Magic' has not been sold or made publicly available more than one year prior to the filing date of the instant application.

SUMMARY

The following traits have been repeatedly observed and represent the distinguishing characteristics of 'Hawaii Magic'. In combination these traits set the new cultivar apart from all others existing varieties of *Leucadendron* known to the inventor. 'Hawaii Magic' has not been tested under all possible conditions and phenotypic differences may be observed with variations in environment, climatic, and cultural conditions, however, without any variance in genotype.

1. 'Hawaii Magic' exhibits a compact bushy plant habit.
2. A two-year old container-grown plant of 'Hawaii Magic' is approximately 65 cm in height and 45 cm to 50 cm in width.
3. The foliage color of 'Hawaii Magic' changes from olive green in summer months to orange-red in the fall and becoming more intensely plum colored towards early spring.
4. 'Hawaii Magic' achieves its most striking foliage color in conditions of full sun.
5. The stems of 'Hawaii Magic' are bright red in color.
6. 'Hawaii Magic' bears only male flowers which are bright yellow in color.
7. 'Hawaii Magic' prefers humus rich, acid, well-drained medium, which is low in phosphorus.

BRIEF DESCRIPTION OF THE PHOTOGRAPHS

The accompanying drawings illustrate the distinguishing traits of the new *Leucadendron* cultivar 'Hawaii Magic'. All plants in the drawings have received one pinch after initial cutting establishment and a second pinch approximately one year later. The plants have been grown without any chemical growth regulators. The drawings were made from digital photographic images. Although colors may appear different from actual colors due to light reflectance, they are as accurate as possible by conventional or digital photography.

FIG. 1 depicts a three-year old plant of 'Hawaii Magic' in April. The plant has been grown out of doors at the inventor's nursery in Kula, Hi. At this time of year, the foliage color of 'Hawaii Magic' is olive green becoming deep purple towards and at the terminal growth.

BOTANICAL DESCRIPTION OF THE PLANT

Figure 1:
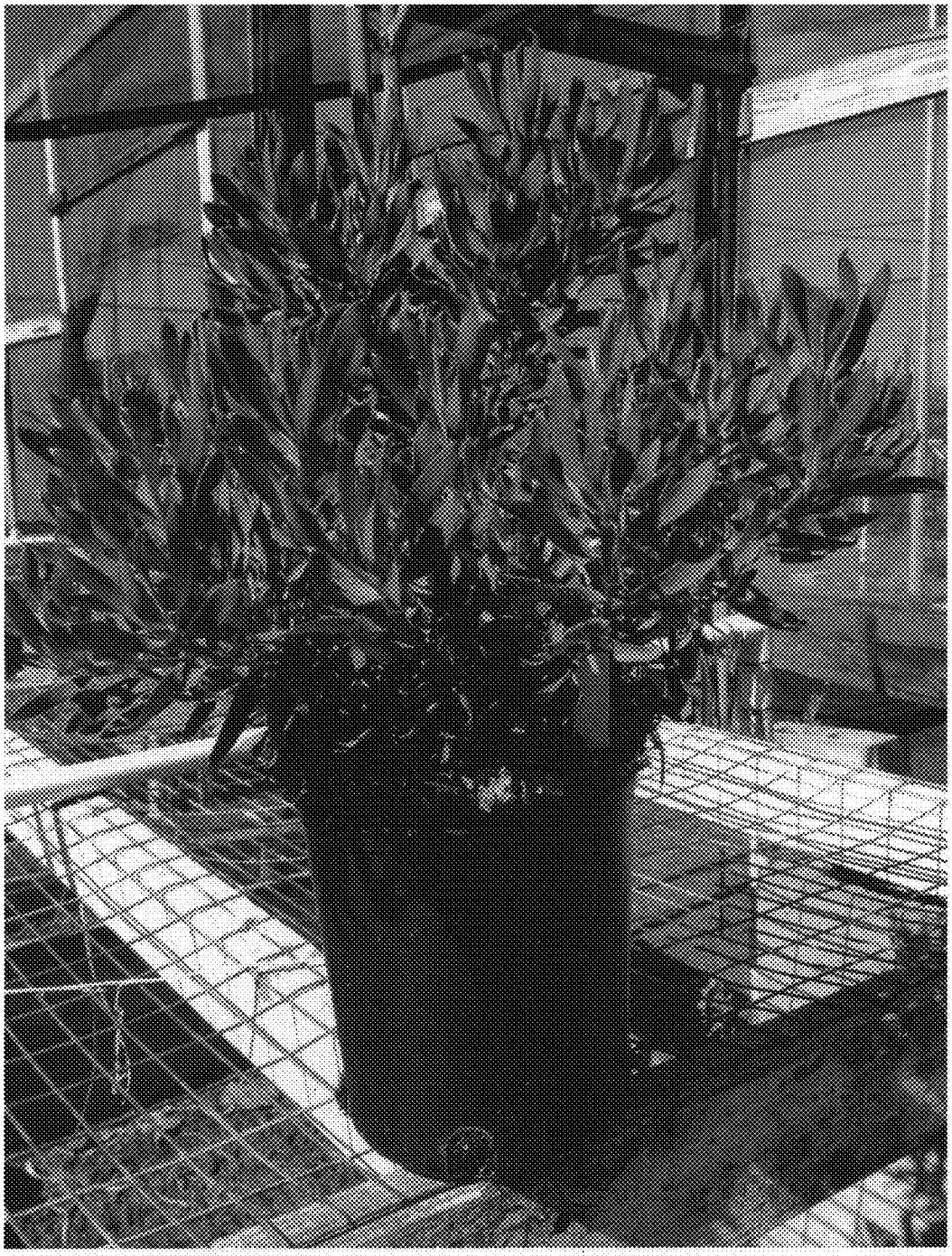
Figure 2:
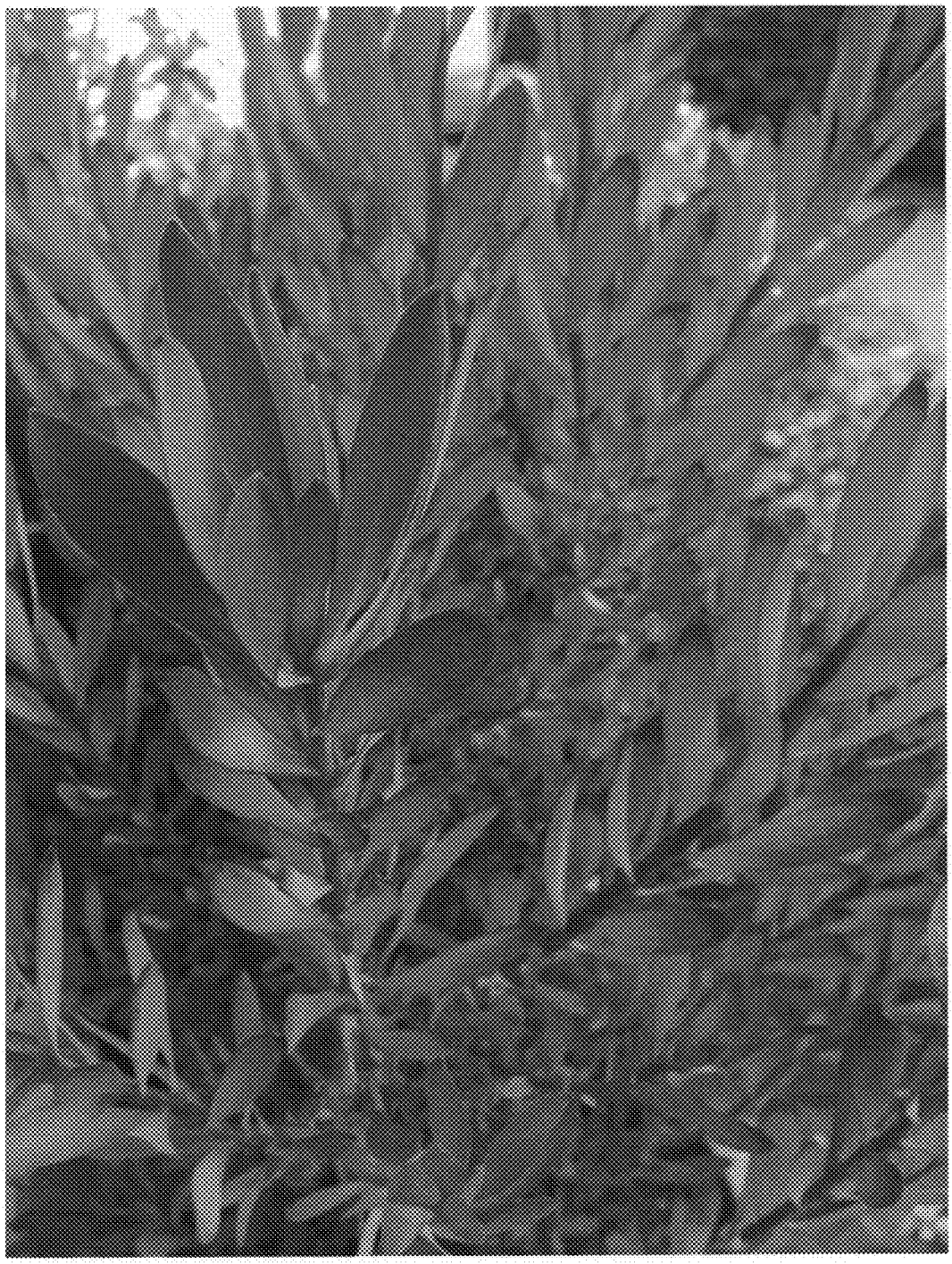
FIG. 2 depicts a close up view of the plum color of the newest terminal shoot growth of 'Hawaii Magic', and the red stems, as exhibited in January.
Figure 3:
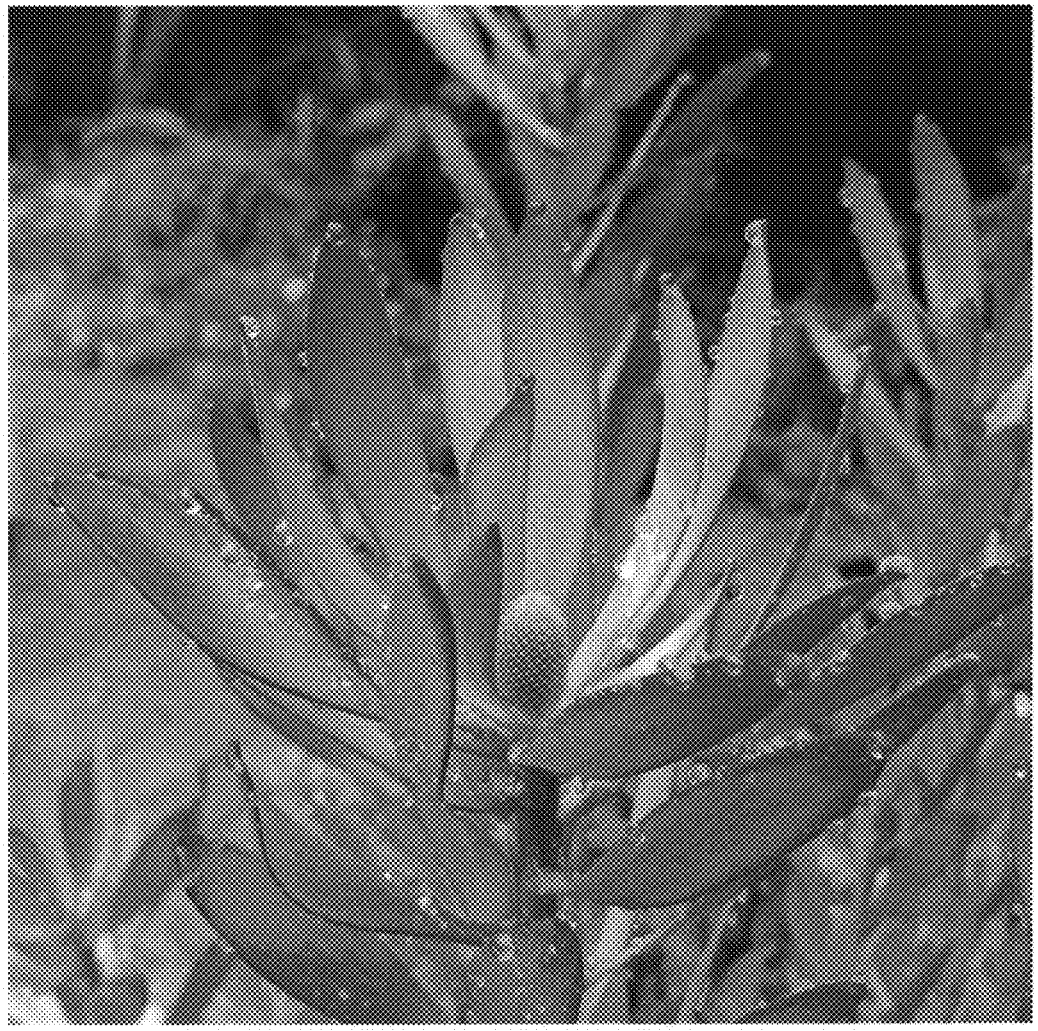
FIG. 3 depicts a close up view of the plum color of the terminal shoot growth of 'Hawaii Magic', and a newly-emerged male flower, as exhibited in February.

The following is a detailed botanical description of the *Leucadendron* plant named 'Hawaii Magic'. Data was collected from a two-year old plant which was growing outdoors in a 3-gallon container in Santa Barbara, Calif. Phenotypic differences may be observed with variation in environmental, climatic, and cultural conditions. The color determinations are in accordance with the 2007 Edition of The Royal Horticulture Society Color Chart except where general color terms of ordinary dictionary significance are used.

Botanical classification:
- *Family*.—Proteaceae.
- *Genus*.—*Leucadendron*.
- *Species*.—*salignum* x *discolor*.
- *Variety*.—'Hawaii Magic'.

Parentage:
- *Male parent*.—*Leucadendron discolor* (species, unpatented).
- *Female parent*.—*Leucadendron salignum* 'Red Devil' (unpatented).

Plant description:
- *Propagation method*.—Semi-ripe tip cuttings.
- *Rooting system*.—Fine and fibrous.
- *Vigor*.—Moderate.
- *Time to develop roots*.—4 to 6 weeks are needed for a cutting to develop roots at recommended rooting temperature of 20° to 22° Centigrade.
- *Crop time*.—Two years are required to produce a full and branched 2-gallon container plant.
- *Use*.—Ornamental for use as a landscape plant or container plant.
- *Type*.—Perennial in USDA Hardiness Zone 8 and higher.
- *Overall dimensions*.—After 2 year's growth in a 2-gallon container: 65 cm in height and 45 cm to 50 cm in width.
- *Cultural requirements*.—Grow in full sun with moderate water, and well-draining soil.
- *Hardiness*.—USDA Zone 8.
- *Growth habit*.—Freely branching bush.
- *Blooming season*.—Male flowers only are produced with first buds appearing in late January and fully developed flowers by late March.
- *Lastingness of blooms*.—4 weeks.

Stem (below first pinch):
- *Length*.—2 cm to 3 cm.
- *Diameter*.—6 mm.
- *Color*.—178A.
- *Shape*.—Round.
- *Texture*.—Smooth.

Branches (after first pinch) and secondary branches (after two pinches):
- *Quantity*.—5 to 6 branches, each 3 to 4 secondary branches.
- *Branch length*.—25 cm to 30 cm, secondary branches 18 cm to 24 cm.
- *Internode length* (*branches and secondary branches*).—1.5 cm to 2.0 cm.
- *Branch stem diameter*.—3 mm to 5 mm.
- *Branch stem shape*.—Round.
- *Branch stem color*.—46A.

Leaves:
- *Type, arrangement*.—Simple, opposite.
- *Attachment*.—Sessile.
- *Quantity per branch*.—Typically, 6 pairs on each branch, 6 pairs on each sub-branch.
- *Shape*.—Oblanceolate.
- *Length*.—60 mm.
- *Width*.—10 mm.
- *Margin*.—Smooth, entire.
- *Thickness*.—Slightly fleshy.
- *Venation*.—Pinnate. Midrib slightly sulcate.
- *Surface texture*.—Smooth, leathery.
- *Color*.—Summer foliage (both surfaces): One-year old leaves: Ranges between N138B and 146D. Current season's new growth: Ranges from and through 42A, 60C and 187C. Winter and spring foliage: Previous summer's old growth: 138C with margins 60C. Previous summer's new growth: 186B to 63A. Some leaves exhibit all colors 138A, 186B, 63A as they age.
- *Apex*.—Acute.
- *Base*.—Cuneate.
- *Fragrance*.—Absent.

Peduncle:
- *Length*.—0.5 cm to 1.5 cm.
- *Shape*.—Round.
- *Diameter*.—2 mm.
- *Texture*.—Smooth, semi-glossy.
- *Color*.—12D.

Inflorescence and flowers: Inflorescence rarely produced until second or third growing season.
- *Inflorescence type*.—Terminal, consisting of a dense cluster of male flowers.
- *Inflorescence shape*.—Cylindricial.
- *Inflorescence dimensions*.—Height 2 cm, diameter 1 cm.
- *Flowers*.—Quantity: Between 600 to 700 solitary flowers per inflorescence. Arrangement: Solitary flowers, tightly packed in cross-diagonal rows, borne on very short pedicels. Pedicel dimensions: 1 mm in length, less than 0.5 mm in diameter. Pedicel color: 11A. Development of Flowers: Flowers first open at base of inflorescence. Final flowers open at apex of inflorescence approximately one week later. Fragrance: None. Persistent or self-cleaning: Persistent. Flower longevity on the plant: Less than one day in color, two to three weeks while persistent. Flower color: 11A, rapidly becoming dark brown 200A and while persistent. Flower basal bracts: 2 to 4 in number, cylindrical, 1.5 mm in length, 1 mm in diameter, appear stunted, color dark brown or black between 200A and 203A.

Buds:

*Number of buds per inflorescence*.—Between 600 and 700.

*Shape*.—Tetragonal.

*Dimensions*.—0.5 mm to 0.75 mm in height and width.

*Color*.—N144B becoming 11A.

Petals:

*Number, arrangement*.—Four, initially fused, ovoid.

*Shape*.—Oblanceolate.

*Margin*.—Smooth, undulating.

*Base*.—Cuneate.

*Apex*.—Emarginate.

*Dimensions*.—2 mm in length, 0.5 mm to 1.0 mm in width.

*Texture* (*both surfaces*).—Smooth, glabrous.

*Color* (*both surfaces*).—11A.

Involucral bracts:

*Arrangement and number*.—Single whorl consisting of 8 uniform involucral bracts and 0 to 2 shorter and narrower malformed bracts.

*Shape*.—Oblanceolate.

*Dimensions*.—45 mm in length, 9 mm in width.

*Margin*.—Smooth, entire.

*Base*.—Truncate.

*Apex*.—Acute.

*Texture*.—Smooth, leathery.

*Color* (*March, adaxial surface*).—64C; margin 64B.

*Color* (*March, abaxial surface*).—163C towards base, becoming 64C towards apex; margin 64B.

Reproductive organs and seed: None observed.

Drought tolerance: Drought tolerant.

Diseases and pests: 'Hawaii Magic' has not been found susceptible or resistant to any particular horticultural pests or diseases.

COMPARISON WITH PARENTAL LINES AND KNOWN VARIETY

'Hawaii Magic' differs from *Leucadendron discolor* by foliage and stem color and by overall size. Whereas 'Hawaii Magic' exhibits bright red stems and leaf colors which range from green to plum, the species *Leucadendron discolor* bears green leaves on green stems. In addition, whereas 'Hawaii Magic' grows to 65 cm in height and 50 cm in width, *Leucadendron discolor* grows to 2 m to 2.5 m in height and 1.5 m in width.

'Hawaii Magic' differs from *Leucadendron salignum* var. 'Red Devil' by foliage color and plant size. Whereas 'Hawaii Magic' exhibits leaf colors which range from green to plum, the leaves of *Leucadendron salignum* var. 'Red Devil' are yellow and red in color. In addition, whereas 'Hawaii Magic' grows to 65 cm in height and 50 cm in width, *Leucadendron salignum* var. 'Red Devil' grows to 1.0 m to 1.5 m in height and 1 m in width.

'Hawaii Magic' may also be compared with the *Leucadendron* variety in commerce known as 'Safari Sunset' (unpatented). In comparison with 'Safari Sunset', 'Hawaii Magic' has a tight compact habit and short internodes compared to the medium to large habit and longer internodes of 'Safari Sunset'. In addition, the foliage color of 'Hawaii Magic' changes through the season whereas the foliage color of 'Safari Sunset' is uniformly green and red all season long.

I claim:

1. A new and distinct cultivar of *Leucadendron* plant named 'Hawaii Magic' as described and illustrated herein.

* * * * *